(12) United States Patent
Satasiya et al.

(10) Patent No.: US 8,080,053 B2
(45) Date of Patent: Dec. 20, 2011

(54) STENT, STENT REMOVAL AND REPOSITIONING DEVICE, AND ASSOCIATED METHODS

(75) Inventors: Pankaj Satasiya, Charlotte, NC (US); Eric K. Mangiardi, Charlotte, NC (US)

(73) Assignee: Merit Medical Systems, Inc., South Jordan, UT (US)

( * ) Notice: Subject to any disclaimer, the term of this patent is extended or adjusted under 35 U.S.C. 154(b) by 591 days.

(21) Appl. No.: 11/496,910

(22) Filed: Aug. 1, 2006

(65) Prior Publication Data

US 2008/0033528 A1    Feb. 7, 2008

(51) Int. Cl.
*A61F 2/06* (2006.01)
(52) U.S. Cl. ....................................................... 623/1.15
(58) Field of Classification Search .................. 606/108; 623/1.11, 1.15, 1.18, 1.32, 11.11, 23.7
See application file for complete search history.

(56) References Cited

U.S. PATENT DOCUMENTS

| | | | |
|---|---|---|---|
| 5,035,706 A | 7/1991 | Giantureo et al. | |
| 5,156,609 A | 10/1992 | Nakao et al. | |
| 5,749,921 A | 5/1998 | Lenker et al. | |
| 5,776,186 A | 7/1998 | Uflacker | |
| 5,897,589 A | 4/1999 | Cottenceau et al. | |
| 5,941,895 A | 8/1999 | Myler et al. | |
| 6,090,129 A | 7/2000 | Ouchi | |
| 6,149,651 A | 11/2000 | Drewry et al. | |
| 6,165,209 A | 12/2000 | Patterson et al. | |
| 6,187,016 B1 | 2/2001 | Hedges et al. | |
| 6,241,757 B1 | 6/2001 | An et al. | |
| 6,273,917 B1 | 8/2001 | Inoue | |
| 6,361,540 B1 | 3/2002 | Gauderer et al. | |
| 6,375,676 B1 | 4/2002 | Cox | |
| 6,607,539 B1 | 8/2003 | Hayashi et al. | |
| 6,676,692 B2 | 1/2004 | Rabkin et al. | |
| 6,679,893 B1 | 1/2004 | Tran | |
| 6,699,277 B1 | 3/2004 | Freidberg et al. | |
| 6,802,846 B2 | 10/2004 | Hauschild et al. | |
| 6,821,291 B2 | 11/2004 | Neisz et al. | |
| 7,175,652 B2 * | 2/2007 | Cook et al. ................... | 623/1.13 |
| 7,252,680 B2 | 8/2007 | Freitag | |
| 2002/0040236 A1 | 4/2002 | Lau et al. | |
| 2002/0058986 A1 | 5/2002 | Landau et al. | |
| 2002/0143387 A1 | 10/2002 | Soetikno et al. | |
| 2002/0188344 A1 | 12/2002 | Bolea et al. | |

(Continued)

FOREIGN PATENT DOCUMENTS

DE    10118944    10/2002

(Continued)

OTHER PUBLICATIONS

Examination Report for EP 04789198 dated Oct. 25, 2007.

(Continued)

*Primary Examiner* — Ryan Severson
*Assistant Examiner* — Ashley Cronin
(74) *Attorney, Agent, or Firm* — Stoel Rives LLP

(57) ABSTRACT

A removable stent for placement within a lumen is provided. The stent includes a scaffolding of struts formed from a tube of memory material and having a proximal end, a distal end, and an interior region. The stent includes at least two flexible elements independently secured to the scaffolding and spaced circumferentially from one another. Each element defines an engageable member such that an inwardly directed force applied to the engageable members reduces a diameter of the scaffolding.

18 Claims, 4 Drawing Sheets

U.S. PATENT DOCUMENTS

| | | |
|---|---|---|
| 2003/0149475 A1 | 8/2003 | Hyodoh et al. |
| 2003/0153970 A1 | 8/2003 | Rao et al. |
| 2004/0116996 A1 | 6/2004 | Freitag |
| 2007/0233230 A1 | 10/2007 | Nissl et al. |
| 2007/0276463 A1 | 11/2007 | Nissl et al. |
| 2008/0033528 A1 | 2/2008 | Satasiya et al. |
| 2008/0140181 A1 | 6/2008 | Reynolds et al. |

FOREIGN PATENT DOCUMENTS

| | | |
|---|---|---|
| DE | 10335948 | 2/2005 |
| EP | 0701800 A1 | 3/1996 |
| EP | 0857471 | 8/1998 |
| EP | 1308138 A2 | 5/2003 |
| JP | 11-057022 | 3/1999 |
| WO | WO 00/44308 | 8/2000 |
| WO | WO 02/083037 | 10/2002 |
| WO | WO 03/022181 | 3/2003 |
| WO | WO 03/096935 | 11/2003 |
| WO | WO 2005/079705 | 9/2005 |

OTHER PUBLICATIONS

International Search Report for PCT/US2004/031886 dated Feb. 7, 2005.
International Search Report for PCT/US2005/038519 dated Apr. 25, 2007.
Office Action issued in U.S. Appl. No. 10/573948 dated Nov. 5, 2009.
Supplementary European Search Report for EP 04789198 dated Apr. 5, 2007.
Office action dated Jun. 24, 2010 for U.S. Appl. No. 10/573,948.
Office action dated Jun. 24, 2010 for U.S. Appl. No. 11/577,859.
Office Action dated Jan. 7, 2011 for U.S. Appl. No. 11/577,859.
Notice of Allowance dated Feb. 16, 2011 for U.S. Appl. No. 10/573,948.
Office action dated Aug. 11, 2011 for U.S. Appl. No. 11/577,859.

* cited by examiner

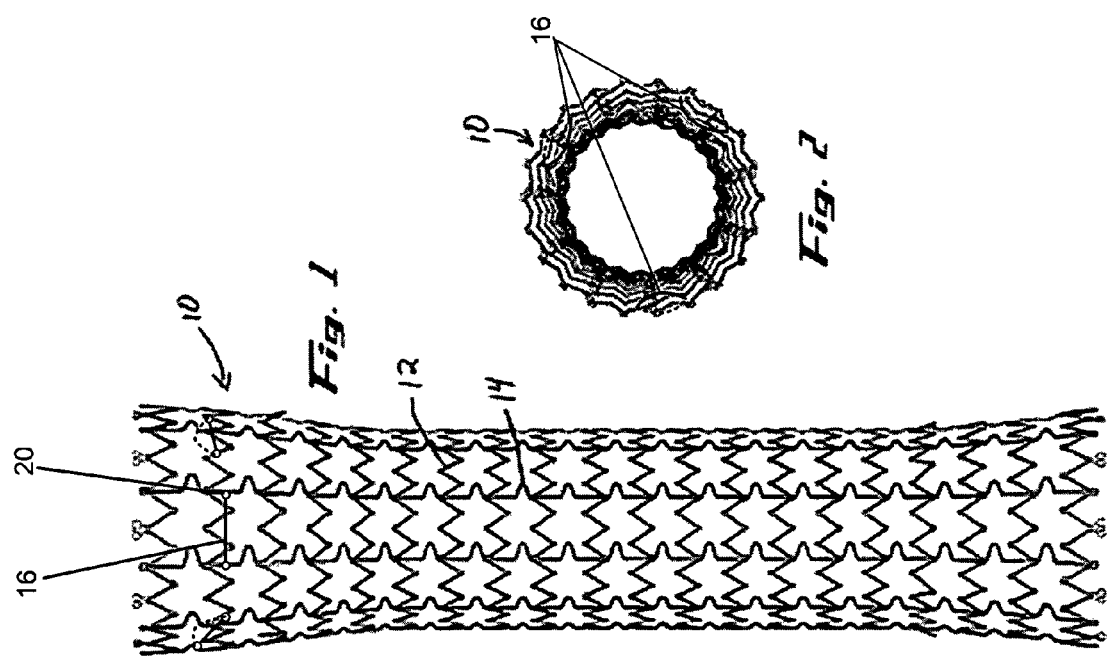

STENT, STENT REMOVAL AND REPOSITIONING DEVICE, AND ASSOCIATED METHODS

BACKGROUND OF THE INVENTION

1) Field of the Invention

The present invention relates to stents, in particular, to a stent removal and repositioning device that promotes removal or repositioning of a stent within a lumen.

2) Description of Related Art

Stents are devices that are inserted into body lumens such as vessels or passages to keep the lumen open and prevent closure due to a stricture, external compression, or internal obstruction. In particular, stents are commonly used to keep blood vessels open in the coronary arteries and they are frequently inserted into the ureters to maintain drainage from the kidneys, the bile duct for pancreatic cancer or cholangiocarcinoma, or the airways and esophagus for strictures or cancer. Vascular as well as nonvascular stenting has evolved significantly; unfortunately there remain significant limitations with respect to the technology for positioning and removing stents following implantation into various portions of a patient's anatomy.

In various areas of application, e.g., bronchus, biliary, trachea, or esophagus, the stents must be removable from the body or repositionable as a function of the course of the disease or treatment. This can be problematic since newly formed tissue can grow on the support frame of the stent and even grow through it, which can result in complications when removing a stent. In this regard, stents have been developed that include a support frame surrounded on the outside by a thread or wire. The support frame can be radially constricted by pulling on the thread ends that are each provided with a loop or the like, creating a "purse-string" effect, which makes it possible for the frame to be removed or repositioned. However, when the wire or thread is guided or braided in multiple windings around the support frame, a high degree of friction results between the two stent components, which has a disadvantageous effect on the explantation process. In addition, stents having eyelets for looping the thread therethrough may have sharp edges that cause the thread to tear or break during the removal process.

Alternatively, physicians have grasped the thread ends with forceps or a similar instrument to reposition or remove the stent from within the lumen. However, this can be complex at times when the tissue has grown over the suture thread. Also, the suture may not be strong enough to remove the stent. Grasping may lead to damage to the stent itself, as the forceps may have difficulty accessing or adequately gripping the thread to remove or reposition the stent. Physicians may also use grasping forceps to grab the struts of the stent at a proximal end and remove the stent from the deployment site, but this also risks damage to the lumen or the stent, as the proximal end of the stent may be difficult to access.

Thus, there is a need in the industry for a stent that reduces the risk of damage to the stent, thread or suture, and/or the surrounding tissue during removal or repositioning of the stent. In addition, there is a need for a stent that provides for greater accessibility, as well as promotes effective repositioning and/or removal of the stent from a lumen.

BRIEF SUMMARY OF THE INVENTION

The present invention addresses the above needs and achieves other advantages by providing a stent that is capable of being repositioned or removed within a lumen. In particular, the stent includes a plurality of engageable members spaced about the circumference of the stent. An inward force applied to the engageable members, such as with a stent removal device, is capable of reducing the diameter or outward radial force of the stent. Each engageable member is individually engaged such that the stent removal device does not "purse string" the stent when engaging the engageable members, and the stent removal device engages the engageable members without directly gripping the stent.

In one embodiment of the present invention, a removable stent for placement within a lumen is provided. The stent includes a scaffolding of struts formed from a tube of memory material and having a proximal end, a distal end, and an interior region. The stent also includes at least two flexible elements independently secured to the scaffolding and spaced circumferentially from one another. In addition, each element defines an engageable member such that an inwardly directed force applied to the engageable members reduces a diameter of the scaffolding.

According to various aspects of the removable stent, each element is intertwined about the scaffolding. One or more eyelets could be positioned at the proximal and distal ends of the stent, and each element could extend through at least one eyelet. Each engageable member may be equidistantly spaced from one another and/or be arranged proximate to the proximal and/or distal ends of the scaffolding. Moreover, at least a portion of each engageable member could extend inwardly into the interior region of the scaffolding. Free ends of each element may be joined together to define a respective engageable member, and/or the free ends of each element may be joined to the scaffolding to define a respective engageable member. Each element could comprise a suture material, and/or the free ends of each element could be joined with a knot. Typically, each knot is positioned outside of the interior region of the scaffolding.

The present invention also provides an additional variation of a removable stent. The removable stent includes at least two elements independently coupled to the scaffolding and spaced circumferentially from one another, wherein each element is coupled to the scaffolding at at least two locations to define an engageable member such that an inwardly directed force applied to the engageable members reduces a diameter of the scaffolding. Moreover, each element may include first and second opposing ends, and at least a portion of each engageable member extending between the first and second ends may extend inwardly into the interior region of the scaffolding. The first and second ends of each element may be joined together to define a respective engageable member, or the first and second ends of each element may be joined to the scaffolding to define a respective engageable member.

Furthermore, embodiments of the present invention provide a further aspect of a removable stent for placement within a lumen. The stent includes a scaffolding of struts comprising a plurality of interconnected legs arranged circumferentially about the stent and a plurality of connectors interconnecting the legs and extending along a longitudinal axis of the stent. The scaffolding has a proximal end, a distal end, and an interior region. The stent also includes at least two elements independently coupled to the scaffolding and spaced circumferentially from one another, wherein each element extends across a plurality of legs and/or connectors to define an engageable member such that an inwardly directed force applied to the engageable members reduces a diameter of the scaffolding.

According to variations of the removable stent, each element includes first and second opposing ends. The first and second ends may be joined to at least one leg and at least one connector, or the first and second ends may be attached to legs or connectors. Moreover, at least a portion of each element may be intertwined circumferentially about the legs and/or connectors.

The present invention also provides a stent removal assembly for removing or repositioning a stent within a lumen where the stent includes a plurality of engageable members defined by respective elements spaced circumferentially from one another about the stent. The assembly includes a tube positioned within the lumen proximate to the stent and a device positioned within the tube that is capable of engaging the engageable members to reduce a diameter of the stent. In one variation of the assembly, the tube is capable of receiving at least a portion of the stent therein. The device includes a plurality of prongs extending within the tube, and a plurality of gripping members at distal ends of respective prongs. The prongs and gripping members are configured to cooperatively bias between a closed position within the tube and an open position outside of the tube, and each gripping member is capable of engaging a respective engageable member in the open position.

In various aspects of the stent removal assembly, each gripping member is capable of engaging a respective engageable member within an interior region of the stent. Each gripping member could engage a respective engageable member proximate to a proximal end of the stent. Furthermore, each gripping member could engage a stirrup member defined by a respective element. The prongs and gripping members may be equidistantly spaced from one another and, in one embodiment of the present invention, the device includes three prongs and associated gripping members.

According to additional variations of the stent removal assembly, the prongs are capable of biasing outwardly as the prongs are moved distally within the tube or as the tube is moved proximally within the lumen. The prongs may bias inwardly as the prongs are moved proximally within the tube or as the tube is moved distally within the lumen. The gripping members may reduce the diameter of the stent as the prongs are biased inwardly.

The present invention provides several advantages. Providing one or more engageable members allows a stent removal device or a similar instrument to engage the engageable members rather than the stent itself. In addition, the stent removal device is relatively incomplex to use, as the prongs and gripping members of the stent removal device are capable of biasing between open and closed positions by simply moving the prongs and gripping members proximally or distally. Moreover, the embodiments of the present invention facilitate easier removal or repositioning of the stent without increasing the likelihood of damage to the stent and/or the lumen. Because the stent removal device engages the engageable members without creating a purse-string effect, the friction created between the engageable members and the scaffolding of the stent is reduced. Furthermore, the engageable members are arranged about the stent to distribute the forces applied during repositioning or removal of the stent, which reduces the risk that the suture and/or stent will be damaged or dislodged.

BRIEF DESCRIPTION OF THE SEVERAL VIEWS OF THE DRAWINGS

Figure 3:
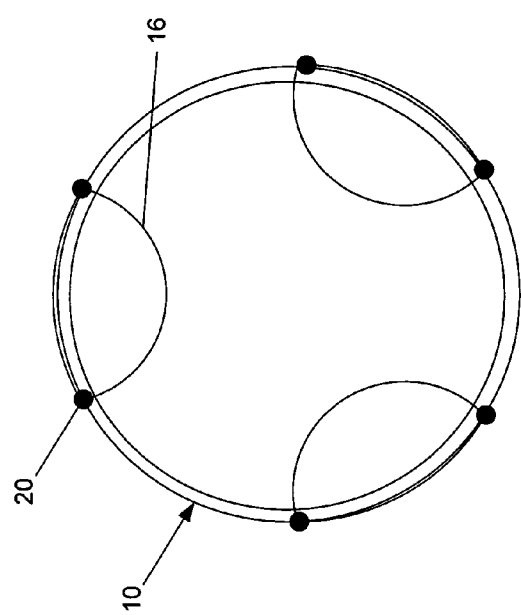
Figure 4:
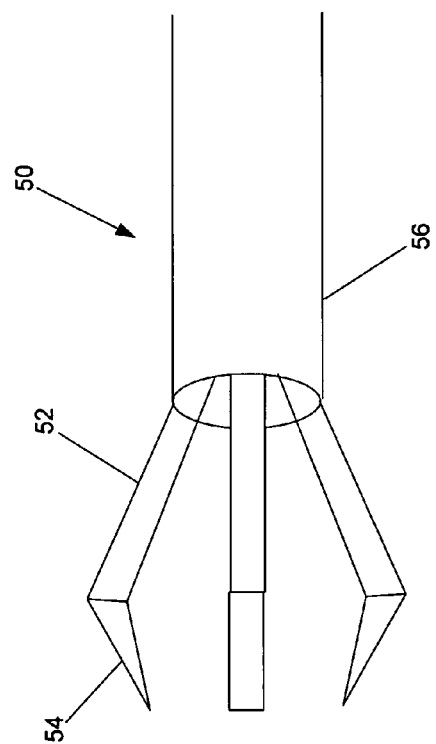
Figure 5:
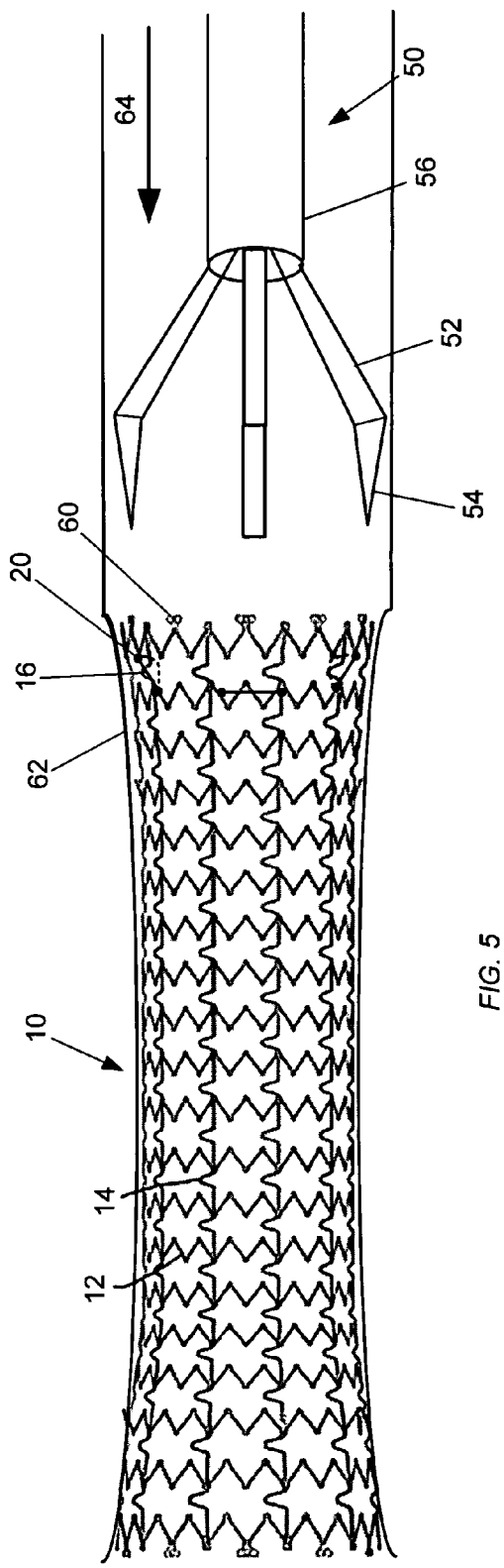
Figure 6:
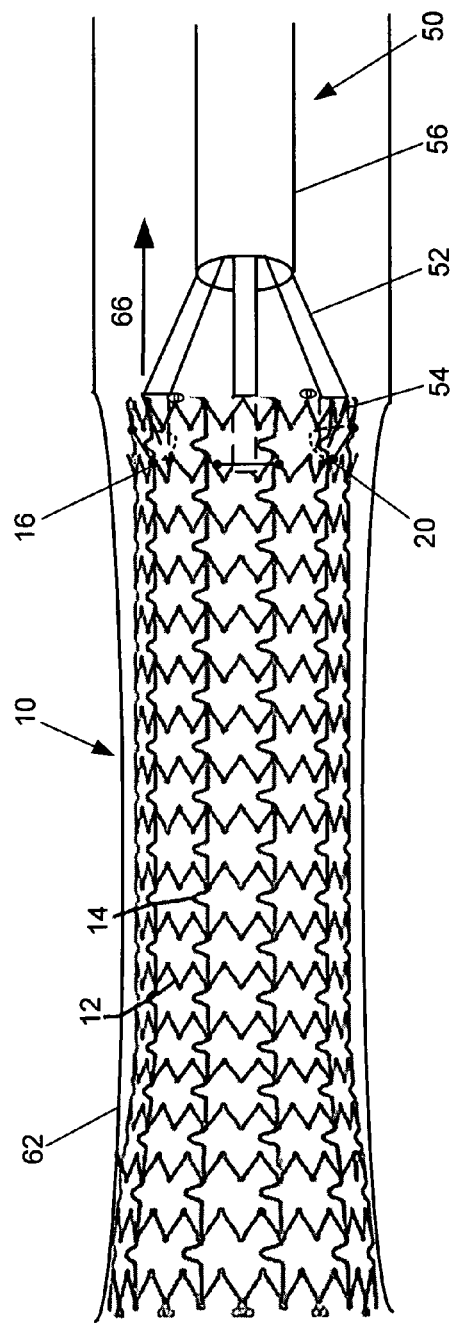
Figure 7:
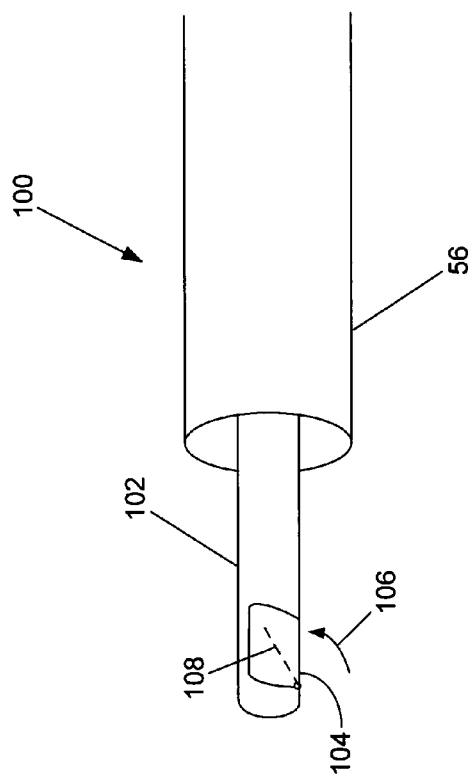
Figure 8:
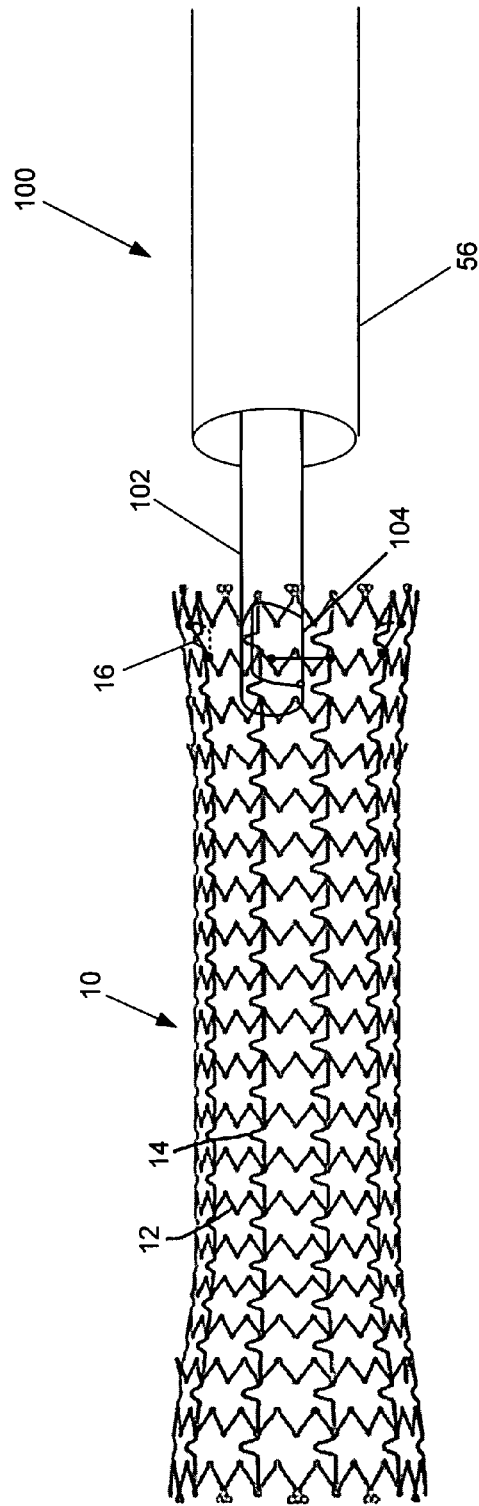

Having thus described the invention in general terms, reference will now be made to the accompanying drawings, which are not necessarily drawn to scale, and wherein:

FIG. 1 is a plan view of a stent having an interstice geometry, according to one embodiment of the present invention;

FIG. 2 is an end view of the stent shown in FIG. 1;

FIG. 3 is an end view of a stent of another embodiment of the present invention including engageable elements for internal gripping and collapsing of the stent;

FIG. 4 is an elevation view of a stent removal device of another embodiment of the present invention for gripping the engageable members of the stent shown in FIG. 3;

FIG. 5 is an elevation view of the stent removal device of FIG. 4 positioned proximate to the stent shown in FIG. 1 and in an open position;

FIG. 6 is an elevation view of the stent removal device of FIG. 4 engaging the engageable elements shown in FIG. 3;

FIG. 7 is an elevation view of a stent removal device according to another embodiment of the present invention; and FIG. 8 is an elevation view of the stent removal device of FIG. 7 engaging the engageable elements shown in FIG. 3.

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

With reference to FIGS. 1-2, a stent 10 is shown having interstice geometry. The stent 10 is capable of being deployed within a lumen of a patient for treating a variety of indications where the lumen has become constricted. The stent 10 includes a plurality of engageable members 16 that are capable of being engaged by a stent removal device 50 for repositioning or removing the stent, as will be explained in further detail below.

The stent 10 includes a scaffolding of struts. The struts generally include a plurality of interconnected legs 12 and connectors 14. As shown in FIG. 1, the stent 10 includes a series of legs 12 arranged circumferentially about the stent, as well as arranged in rows along the longitudinal axis of the stent, while a plurality of connectors 14 are arranged parallel to the longitudinal axis of the stent to connect the rows together. The stent 10 is formed of a memory metal that facilitates flexibility of the stent 10 such that the stent may be deformed and return to its original shape. As such, the legs 12 and connectors 14 of the stent 10 are preferably formed from a composite material such as Ni, C, Co, Cu, Cr, H, Fe, Nb, O, Ti and combinations thereof (e.g., Nitinol). The composite material is generally formed into a compressed tube from which the stent is etched and is formed on a suitable shaping device to give the stent the desired external geometry.

The stent 10 is generally cylindrical, having openings at the proximal and distal ends. As illustrated in FIG. 1, the diameter of the proximal and distal ends is slightly larger than the diameter of longitudinal portion of the stent extending therebetween. In the event the stent is to be shaped to the dimensions of a particular lumen, optical photography and/or optical videography of the target lumen may be conducted prior to stent formation. The interstice geometry of the stent then can be etched and formed in accordance with the requirements of that target lumen. For example, if the stent 10 were designed for the trachea, which has a substantially D shaped lumen and additionally the middle portion of the stent is preferably softer than the proximal or distal ends, the stent could be designed to those specifications. In particular, if the topography of the trachea of a particular patient is captured optically and the appropriate dimension provided, a patient specific prosthesis could be engineered. These techniques can be adapted to other non-vascular lumina but is very well suited for vascular applications where patient specific topography is a function of a variety of factors such as genetics, lifestyle, etc.

It should be pointed out that, unlike the use of differing shape memory materials to change regions of a stent 10, stents in accordance with the present invention can take on various characteristic combinations of interstice geometry by changing angles, segment lengths, and segment thicknesses during the etching and forming stages of stent engineering or during post formation processing and polishing steps. Moreover, by modifying the geometry of the connectors 14, additional functionality may be achieved.

The stent could also include a cover, typically a polymer such as polyurethanes (e.g., polycarbonate urethane, or Chronoflex® manufactured by Cardiotech International), that is applied between the legs 12 and connectors 14 to provide a predetermined shape for the stent 10, as well as graft each of the legs and connectors into a unitary structure. The cover does not inhibit flexing or radial expansion of the stent 10, although it is possible to design the cover so that it controls the physical properties of the stent.

The cover is typically applied to the scaffolding using a dipping process. The cover forms a thin layer over the scaffolding such that a portion of the scaffolding is raised above the surface of the cover within the openings between the legs 12 and connectors 14. However, the interior of the stent remains substantially smooth. Providing a raised scaffolding promotes cilia action by allowing cilia movement between stent 10 struts, while a smooth interior surface promotes fluid flow through the interior region of the stent and prevents tissue ingrowth into the stent.

The engageable members 16 may be any suitable element capable of being engaged by the stent removal device 50. For example, the engageable members 16 could be a suture material, as known to those skilled in the art, such as polypropylene. However, it is understood that the term "suture," as used herein, could be any suitable thread or wire capable of transferring force from the stent removal device 50 to the stent 10 in alternative embodiments of the present invention. Thus, the engageable members 16 could be various metallic, polymeric, or combinations of materials that may be engaged by the stent removal device 50 to remove or reposition the stent within the lumen, as will be explained in further detail below.

Therefore, it is understood that any number of configurations of stents 10 could be incorporated and still be within the present scope of the invention. An exemplary embodiment of the interstice geometry of a stent 10 is disclosed in U.S. Patent Publication No. 20040127973 (application Ser. No. 10/674,972), entitled "Removable Biliary Stent," which is assigned to the present assignee and is incorporated herein by reference. Thus, the interstice geometry of the stent 10 should not be limited to that depicted in the disclosed Figures, as any number of configurations of interstice geometry could be employed with the present invention to achieve various degrees of rigidity and functionality. U.S. Patent Publication No. 20040122511 (application Ser. No. 10/669,450) entitled "Coated Stent with Geometry Determined Functionality and Method of Making the Same," which is assigned to the present assignee, is also incorporated herein by reference, and further describes a cover that may be employed with the present invention, including the types of materials and properties suitable for the cover, as well as the process of manufacturing the stent 10.

In one embodiment of the present invention, the stent 10 includes engageable members 16 configured as loops of suture that extend as stirrups or loops around the outside of the stent and into an interior region of the stent, as shown in FIG. 3. The loops of suture 16 may extend or be interwoven through interstices between the legs 12 and connectors 14 of the stent 10 and attach at knots 20 that help ensure the stirrup length is maintained. Alternatively, the engageable members 16 could be interwoven through eyelets 60 located at the proximal and/or distal opening of the stent 10. In addition, the engageable members 16 could be a polymeric or metallic material or some other composition to form the stirrup. Suture, however, has the advantage of lying flat for the passage of food or other debris through the opening of the stent 10 due to its flexibility.

Also, the engageable members 16 could be attached through welding or gluing, in lieu of, or in addition to, knots 20. In addition, the engageable members 16 could be attached directed to the legs 12 and/or connectors 14 of the stent such that the engageable members are semi-circular in configuration and only extend within the interior region of the stent. Although the knots 20 secure the engageable members 16 to the stent 10 and help maintain the length of the engageable members, the engageable members could also be continuous loops of material that extend through interstices of the stent 10. When knots 20 are employed to attach the free ends of the engageable members 16, the knots are preferably positioned proximate to the outer surface of the stent 10. Thus, the knots 20 are positioned outside of the interior region of the stent 10 to prevent any disturbance in fluid flow through the stent.

Thus, the term "engageable member" is not meant to be limiting, as the engageable members could be stirrups, loops, or other configurations, where at least a portion of the engageable members extends inwardly into the interior region of the stent and returns back to couple to itself or the stent. The engageable members may be various shapes and sizes (e.g., circular or semi-circular) as long as the engageable members are capable of being engaged by a stent removal device 50.

One, two, three (in the illustrated embodiment of FIG. 3), or more engageable members 16 are formed by the elements (e.g., suture) and are generally equidistantly spaced about the proximal opening of the stent 10. For instance, three engageable members 16 could be spaced approximately 120° apart about the circumference of the stent 10. Equidistantly spacing the engageable members 16 about the proximal opening of the stent 10 allows the stent to be symmetrically collapsed, at least partially and without purse-stringing, by grabbing the engageable members. However, the engageable members 16 could be arranged various distances from one another and could be located proximate to the proximal and/or distal openings of the stent 10.

In the embodiment illustrated in FIG. 3, the engageable members 16 are grasped internally by a stent removal device 50, as shown in FIG. 4. The stent removal device 50 is operable to engage each of the engageable members 16 and at least partially collapse the proximal end of the stent 10. The stent removal device 50 includes a plurality of prongs 52 having a respective gripping member 54 at each of its distal ends. The prongs 52 and gripping members 54 are capable of sliding into and out of a catheter 56, while the gripping members can be positioned to engage the engageable members 16. The stent removal device 50 of the present invention could also include hooked ends for firmer gripping and more or fewer prongs 52 and gripping members 54 may be employed. A plurality of engageable members 16 (e.g., six engageable members) have the advantage of providing more options for gripping, collapsing, and moving the stent 10. For example, although the stent 10 may include six engageable members 16, the stent removal device 50 is capable of grabbing different combinations of engageable members, such as any three engageable members.

As shown in FIG. 4, the prongs 52 extend angularly outward as the prongs are moved out of the catheter 56. The prongs 52 are configured to expand outwardly as the prongs are moved distally out of the catheter 56, or as the catheter is moved proximally. In this regard, because the prongs 52 are compressed within the catheter 56 in a pre-loaded configuration (i.e., closed position), the catheter restrains the prongs 52 therein and, as the prongs are moved out of the catheter, the prongs bias outwardly. Similarly, as the prongs 52 are moved proximally, or as the catheter 56 is moved distally, the prongs will bias against the catheter, causing the prongs to retract inwardly. Thus, when the gripping members 54 are positioned to engage the engageable members 16, movement of the prongs 52 proximally, or the catheter 56 distally, will result in compressing (i.e., overcoming the outward radial force of the stent 10) the region of the stent proximate to the engageable members such that the diameter of the stent is reduced. The prongs 52 will typically expand to a predetermined diameter when positioned outside of the catheter 56.

FIGS. 5 and 6 illustrate the use of the stent removal device 50 to remove or reposition a stent 10 positioned within a lumen 62. As depicted in FIG. 5, the prongs 52 and gripping members 54 are initially positioned within the catheter 56 and moved distally (i.e., direction 64) out of the catheter such that the prongs and gripping members may expand to a predetermined or desired diameter. The prongs 52 and gripping members 54 are moved proximate to the proximal opening of the stent 10 and positioned to engage respective engageable members 16 (e.g., positioning each gripping member within a respective loop of suture within the interior of the stent, wherein the portion of the engageable members extending into the interior of the stent is shown as hidden lines). When the gripping members 54 are positioned to engage the engageable members 16, the prongs 52 may be retracted in a proximal direction (i.e., indicated by arrow 66) to overcome the radial force of the stent to partially collapse the proximal end of the stent in a radial direction, as shown in FIG. 6. However, the catheter 56 could be moved distally while the gripping members 54 engage the engageable members 16 to overcome the outward radial force of the proximal end of the stent 10. Thus, retracting the prongs 52 within the catheter 56 in a proximal direction causes the prongs to bias against the tube and move the gripping members 54 inwardly. The prongs 52 and gripping members 54 may be retracted further until the proximal end of the stent has collapsed to approximately the diameter of the catheter 56. In this regard, the proximal end of the stent 10 may be reduced to a generally conical shape that may be positioned within the catheter 56. The distal end of the catheter 56 could be a funnel shape that may readily receive the proximal end of the stent 10 but could be generally cylindrical or other shapes to receive the stent therein. While partially positioned within the catheter 56, the stent 10 could be repositioned within the lumen 62. As the prongs 52 and gripping members 54 are moved further proximally within the catheter 56, or as the catheter is moved distally within the lumen 62, the entire stent can be inserted within the catheter for removal from the lumen.

FIG. 7 illustrates an additional embodiment of the present invention. In particular, FIG. 7 shows that the stent removal device 100 includes a longitudinal member 102 and a hook member 104 pivotably coupled to the longitudinal member. The hook member 104 is capable of pivoting inwardly in response to an inwardly applied force but unable to pivot outwardly away from the longitudinal member 102. For example, pivoting the hook member 104 in the direction indicated by arrow 106 causes the hook member to pivot to an inward position, such as that depicted by dotted line 108. The hook member 104 could be spring loaded (e.g., a torsion spring), and the stent removal device 100 could include a stop member (not shown) that prevents the hook member from pivoting outwardly. In this regard, the hook member 104 is capable of engaging an engageable member 16 by positioning the hook member proximate to an engageable member and applying a force to the engageable member to cause the hook member to pivot inwardly. The longitudinal member 102 could be positioned within the loop formed by the engageable member prior to engaging the engageable member 16, or the longitudinal member could be positioned proximate to the engageable member prior to engaging the engageable member. Thus, the configuration of the hook member 104 prevents the engageable member 16 from becoming disengaged after engaging an engageable member.

Thus, as shown in FIG. 8, a portion of the longitudinal member 102 extends outwardly from the catheter 56 and within the stent 10 and engages an engageable member 16 such that the engageable member is incapable of becoming disengaged from the hook member 104 when moving the longitudinal member proximally within the catheter. Furthermore, in order to at least partially collapse the proximal end of the stent 10, the hook member 104 could be manipulated to engage more than one engageable member. Thus, engaging more than one engageable member 16 with the hook member 104 causes the proximal end of the stent 10 to collapse to a sufficient diameter to fit within the distal end of the catheter. The stent removal device 100 is generally used to position at least the proximal end of the stent 10 within the catheter 56 to remove the stent from the lumen.

The present invention provides several advantages. Providing one or more engageable members 16 allows a stent removal device 50 or a similar instrument to engage the engageable members rather than the stent 10 itself. In addition, the stent removal device 50 is relatively incomplex to use, as the prongs 52 and gripping members 54 of the stent removal device are capable of biasing between open and closed positions by simply moving the prongs and gripping members proximally or distally. Moreover, the embodiments of the present invention facilitate easier removal or repositioning of the stent 10 without increasing the likelihood of damage to the stent and/or the lumen. Because the stent removal device 50 engages the engageable members 16 without creating a purse-string effect, the friction created between the engageable members and the scaffolding of the stent is reduced. Furthermore, the engageable members 16 are arranged about the stent 10 to distribute the forces applied during repositioning or removal of the stent, which reduces the risk that the suture and/or stent will be damaged or dislodged.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A removable stent for placement within a lumen in a body of a patient, comprising:
   a scaffolding of struts formed from a tube of memory material and having a proximal end, a distal end, and an interior region; and
   at least two flexible elements independently secured to the scaffolding and spaced circumferentially from one another, wherein free ends of each flexible element are attached at separate locations along the circumference of the scaffolding of struts, wherein each element consists of a suture material and defines an engageable member that is configured to rotate relative to a wall of the lumen from a first position extending inwardly into the interior region of the scaffolding of struts to a second position that is flat and lying flush against an interior surface of the stent, the engageable members configured to reduce a diameter of the scaffolding in response to an inwardly directed force applied to the engageable members in a direction transverse to a longitudinal axis of the lumen, wherein when the removable stent is deployed and in an expanded state within a lumen in the body of the patient, the engageable members extend into the interior region of the scaffolding of struts in the first position and rotation of the engageable members from the first position to the second position is in response to a flow of fluid internal to the body through the lumen.

2. The stent according to claim 1, wherein each element is intertwined about the scaffolding.

3. The stent according to claim 1, further comprising at least one eyelet positioned at the proximal and distal ends of the stent, wherein each element extends through at least one eyelet.

4. The stent according to claim 1, wherein each engageable member is equidistantly spaced from one another.

5. The stent according to claim 1, wherein each element is arranged proximate to at least one of the proximal and distal ends of the scaffolding.

6. The stent according to claim 1, wherein free ends of each element are attached to the scaffolding of struts with a knot.

7. The stent according to claim 6, wherein each knot is positioned outside of the interior region of the scaffolding.

8. A removable stent for placement within a lumen in a body of a patient, comprising:
   a scaffolding of struts formed from a tube of memory material and having a proximal end, a distal end, and an interior region; and
   at least two flexible elements independently coupled to the scaffolding and spaced circumferentially from one another, wherein each element consists of a suture material and has free ends that are coupled to the scaffolding at separate locations along the circumference of the scaffolding of struts to define a plurality of engageable members that are flexible and extend inwardly into the interior region of the scaffolding of struts in a first position, wherein when the removable stent is deployed and in an expanded state within a lumen in the body of the patient the engageable members are configured to rotate relative to a wall of the lumen from the first position to a second position that is flat and lying flush with an interior surface of the stent in response to a flow of material through the lumen, and wherein the engageable members are configured to reduce a diameter of the scaffolding when an inwardly directed force is applied to the engageable members in a direction transverse to the longitudinal axis of the lumen.

9. The stent according to claim 8, wherein each engageable member is equidistantly spaced from one another.

10. The stent according to claim 8, wherein each element is arranged proximate to at least one of the proximal and distal ends of the scaffolding.

11. The stent according to claim 8, wherein each element includes first and second opposing ends.

12. The stent according to claim 11, wherein at least a portion of each engageable member extending between the first and second ends extends inwardly into the interior region of the scaffolding.

13. The stent according to claim 11, wherein the first and second ends of each element are joined to the scaffolding to define a respective engageable member.

14. The stent according to claim 8, wherein the scaffolding of struts comprises a plurality of interconnected legs arranged circumferentially about the stent and a plurality of connectors interconnecting the legs and extending along a longitudinal axis of the stent, and wherein each element extends across at least one of a plurality of legs or connectors.

15. The stent according to claim 14, wherein each element comprises first and second opposing ends.

16. The stent according to claim 15, wherein the first and second ends are joined to at least one of the legs and at least one of the connectors.

17. The stent according to claim 15, wherein the first and second ends are attached to a plurality of legs or a plurality of connectors.

18. The stent according to claim 14, wherein at least a portion of each element is intertwined circumferentially about at least one of a plurality of legs or connectors.

* * * * *